United States Patent [19]

Hanners

[11] Patent Number: Plant 5,421

[45] Date of Patent: Mar. 26, 1985

[54] APPLE TREE—"EVE'S DELIGHT"

[76] Inventor: Daniel A. Hanners, P.O. Box 475, Hood River, Oreg. 97031

[21] Appl. No.: 464,599

[22] Filed: Feb. 2, 1983

[51] Int. Cl.[3] ..... A01H 5/00

[52] U.S. Cl. ..... Plt./35

[58] Field of Search ..... Plt./35

*Primary Examiner*—James R. Feyrer

*Attorney, Agent, or Firm*—Frank B. Robb

[57] ABSTRACT

An Apple variety which may be classified as a striped or partially red variety, similar in color, shape and type to the Delicious variety having large size, disease resistance and better taste as compared with Yellow Newtown, the tree being vigorous, upright, but spreading with good crotch angles, adapting well to leader training.

5 Drawing Figures

BACKGROUND AND DESCRIPTION OF THE INVENTION

The present invention relates to a new and distinct variety of Apple tree, which produces apples similar in color, shape and type to "Spokane Beauty" an unpatented, striped partially red variety of Delicious type, said unpatented variety being one with which I am generally familiar and have grown from time to time.

My new variety has a number of distinctive aspects however, including size of fruit which is one of the characteristics which first brought it to my attention since it was extra large, growing on a terminal bud on a tree of a variety which is known as "Spokane Beauty" (unpatented) and which was observed by me during an inspection of my orchard at Hood River, Oreg.

Carefully preserving the necessary material for reproduction, I have in fact carried out asexual reproduction by budding at my orchard and found that the initial size is maintained through successive propagations and in addition other characteristics are likewise reproduced, including fruit having less scab, mildew and bitter pit when compared with Yellow Newtown (unpatented) and a Golden Delicious which is not a patented variety as far as I am aware.

The Tree upon which the apples of my disclosure are grown also includes some aspects which are valuable commercially, including the fact that the tree is quite vigorous, upright but spreading with good crotch angle and adapts well to central leader training.

While I make no claim to color per se, it is notable that the colors are quite like those Delicious of the striped or partially red variety as classified by color requirements in U.S. Standards for grades of apples and particularly comparable to "Spokane Beauty" the unpatented variety referred to heretofore.

My new variety produces fruit for first picking in late September about the 25th and the last picking in October about the 10th usually.

In summary it may be stated that my new variety is distingushable by the following characteristics:

1. Large size as compared with "Spokane Beauty" (unpatented.)
2. Resistance to scab and mildew.
3. Less tendency to bitter pit.
4. Tree is vigorous, upright but spreading with good crotch angle.
5. Tree adapts well to central leader training.

6. The fruit color is attractive similar to the striped Delicious.

BRIEF DESCRIPTION OF THE DRAWING

The accompanying drawing shows, FIGS. 1–4, typical fruit of my new variety, in several aspects, including the typical lower end with the protuberances notable of Delicious apples, a top disclosure, as well as a full side view and sectional view illustrating the seed and other aspects of the shape. The second sheet (unnumbered) depicts branching habit of the tree.

Eve's Delight, the apple disclosed herein, is a fruitful tree with annual crops under commercial type husbandry. The blossoms usually open in this area, around Hood River, Oreg., one day after Starkrimson Red Delicious and one day before Golden Delicious. Full bloom date in this area will average on or about April 26. The blossoms have approximately the same resistance to spring frost during the blossom period as the Yellow Newtown which is known to withstand two to three degrees colder temperature than most strains of Red Delicious.

Figures 1, 2, 3, 4:
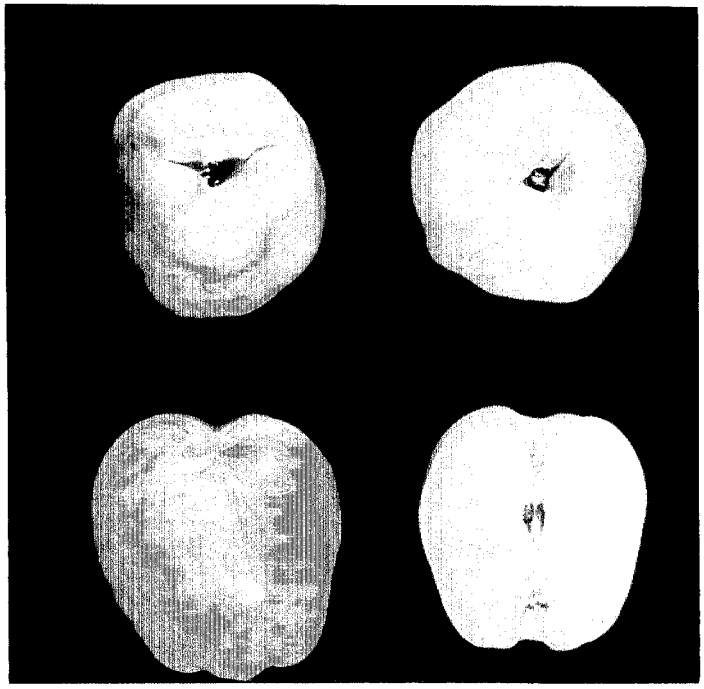

Eve's Delight, is polinated successfully with pollen from Red Delicious, Yellow Newtown and Golden Delicious, and like Yellow Newtown is somewhat self fertile but in limited experiments which I have carried on, the fruit does not seem to grow as well as when it has been invigorated by cross-polination with another variety.

In describing the ground color of Eve's Delight, it is noted that it is almost identical to the original striped Delicious, introduced by Stark a number of years ago. The ground color starts changing from green to greenish yellow approximately 145 days from full bloom and should be picked 145 to 155 days from full bloom for best storage life.

The calyx will retain its green ground color until the fruit is past optimum maturity. The balance of the apple's ground color will hold its greenish-yellow color to past optimum maturity which in the case of larger apples under good cold storage conditions is approximately 120 days after harvest.

The smaller apples (20 ounces and under) may be stored for a longer period with a maximum storage life of approximately 140 days.

The loss of chlorophyl from the ground color is not great during the optimum storage life.

There is shown in the drawing, a view of a tree taken during the winter time, to disclose the distinctive branching habit upright and spreading with good crotch angles.

There follows a detailed description of my new variety, with color terminology where applicable and where used from the Munsell Color Cascade published by MacBeth Kolmorgen Corporation, the color terminolgy being that related to said color cascasde and only other terminology being used where general color terms of ordinary dictionary significance are appropriate.

It is notable that the method of asexual propagation effected by me is by what is known as the budding technique.

Locality where grown and observed: Hood River, Oreg.

Date of first picking: Sept. 25.

Date of last picking: Oct. 10.

Tree: Medium size; vigorous; upright; spreading; tall; round form; rapid growing; hardy; very productive; regular bearer.

*Trunk.*—Stocky; medium.

*Branches.*—Thick; smooth; medium branching. Color — Gray. Lenticels — medium number.

Foliage:

*Leaves.*—Medium (about 4 in. long — 3 in. wide); wide ovate, abruptly pointed; thick. Color — upper 21-15; lower 23-11. Margin — finely serrate. Petiole — Length ($1\frac{3}{8}''$); medium; thick.

Flowers:

*Dates of first and full bloom.*—First about Apr. 18 and full bloom Apr. 26th.

*Size.*—Large.

*Color.*—Pink.

Fruit:

*Maturity when described.*—Eating hard, Sept. 25. Date for optimum storage life should be about 120 to 125 days from full bloom generally.

*Size.*—Variable. Axial diameter $4\frac{1}{2}$ inches. Transverse 5 inches

*Form.*—Uniform; unsymmetrical; irregular; conical; ribbed.

*Cavity.*—Unsymmetrical; Acute; Pubescent toward apex.

*Depth.*—About 1 inch.

*Breadth.*—About 1 inch.

*Basin.*—Unsymmetrical; abrupt; wide base; pubescent.

*Stem.*—Stout; pubescent. Length — About $\frac{3}{8}$th inches.

*Calyx.*—Open; segments persistent; ovate; acuminate; Length — about 3/16ths inches; Separated — ascending; converse from base toward center; Outer surface — glabrous. Inner surface — pubescent

*Eye.*—Large; open.

*Skin.*—Thick; tender; smooth; glossy.

*Dots.*—Obscure and few; small; even; circular.

*Color of dots.*—Light and dark and scattered distribution.

*Ground color.*—23-4.

*Overall appearance.*—38-8.

*Color markings.*—Striped; self colored; bright; red.

*Bloom.*—White.

*General color effect.*—Similar to striped delicious.

Flesh: Juicy.

*Color.*—White with yellowish greenish tint.

*Texture.*—Firm; crisp.

*Flavor.*—Sub acid; sprightly.

*Aroma.*—Distant.

*Quality.*—Good.

Core:

*Sessile.*—Median.

*Bundle area.*—Ovate; cordate; symmetrical.

*Halves of area.*—Equal.

*Bundles.*—Yellowish color.

*Core lines.*—Meeting.

*In cross-section.*—Indistinct.

*Calyx.*—Pubescent; urn shaped. Stem of funnel — long. Depth of tube to shoulder 1 inch. Entire depth — $1\frac{1}{2}$ inches. Styles — present; pubescent.

*Stamens.*—In one area.

*Auxiliary cavity.*—Wanting.

*Seed cells.*—Open.

*Cell walls.*—Thin; tough. Length — $1\frac{1}{8}$th inch. Breadth — $\frac{1}{2}$ inch. Longitudinal section — Ovate; mucronate. Surface — smooth. Cross-section — broad.

Seeds:

*Number perfect.*—19.

*Number imperfect.*—1.

*Largest number in one cell.*—4.

*Length.*—5/16th inch.

*Breadth.*—3/16th inch.

*Form.*—Acute.

*Color.*—Redish brown.

Use: Local; dessert; culinary, special gifts.

Keeping quality: Medium about 120 days in ordinary cold storage.

Resistance to: Insects and diseases both good; shows less scab, mildew and bitter pit when compared with "Yellow Newtown" and Golden Delicious.

I claim:

1. A new and distinct variety of Apple tree substantially as herein shown and described, characterized particularly as to novelty by the unique combination of very large fruits, attractive color similar to striped or partially red Delicious variety, fruit having resistance to scab and mildew, with less bitter pit as compared to Yellow Newtown and Golden Delicious, the tree being vigorous, upright but spreading and having good crotch angles, adapting well to central leader training.

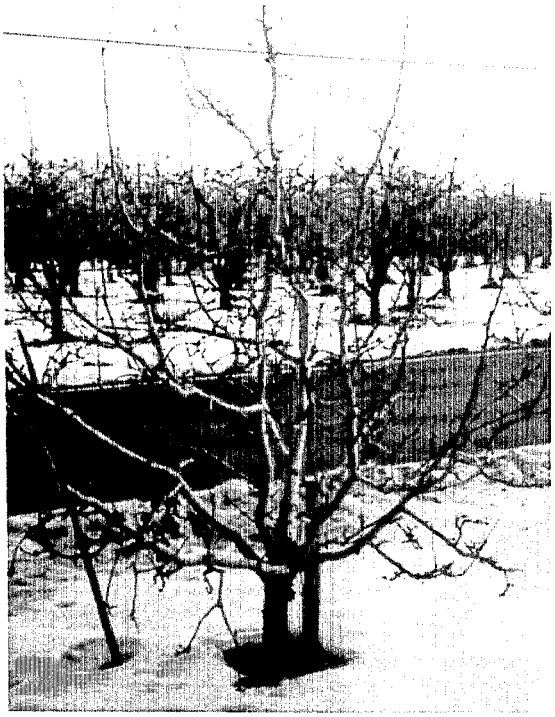

* * * * *